(12) United States Patent
Kirchhofer et al.

(10) Patent No.: US 7,828,779 B2
(45) Date of Patent: *Nov. 9, 2010

(54) INJECTION APPARATUS WITH AN END POSITION-BLOCKED DOSAGE SETTING MEMBER

(75) Inventors: Fritz Kirchhofer, Sumiswald (CH); Michael Schaer, Deitingen (CH); Christoph Sommer, Ramsei (CH)

(73) Assignee: TecPharma Licensing AG, Burgdorft (CH)

( * ) Notice: Subject to any disclaimer, the term of this patent is extended or adjusted under 35 U.S.C. 154(b) by 367 days.

This patent is subject to a terminal disclaimer.

(21) Appl. No.: 10/871,886

(22) Filed: Jun. 18, 2004

(65) Prior Publication Data

US 2005/0033224 A1 Feb. 10, 2005

Related U.S. Application Data

(63) Continuation of application No. PCT/CH02/00684, filed on Dec. 11, 2002.

(30) Foreign Application Priority Data

Dec. 21, 2001 (DE) .................................. 101 63 328
Jun. 11, 2002 (DE) ............................. 202 09 051 U (51) Int. Cl.
*A61M 5/00* (2006.01)

(52) U.S. Cl. ...................................... 604/207; 604/211
(58) Field of Classification Search .................. 604/211, 604/207
See application file for complete search history.

(56) References Cited

U.S. PATENT DOCUMENTS 4,592,745 A 6/1986 Rex et al.
4,865,591 A * 9/1989 Sams .......................... 604/186
4,973,318 A 11/1990 Holm et al.
5,026,343 A 6/1991 Holzer (Continued)

FOREIGN PATENT DOCUMENTS

DE 4112259 A1 10/1992

(Continued)

*Primary Examiner*—Kevin C Sirmons
*Assistant Examiner*—Deanna K Hall
(74) *Attorney, Agent, or Firm*—Dorsey & Whitney LLP; David E. Bruhn, Esq.

(57) ABSTRACT

An injection device including a housing with a reservoir for an injectable product, a delivery device used to dispense a product dose from the reservoir, and a dose metering member which, in order to select the product dose, can carry out a rotational displacement in relation to the housing in a first direction until it reaches an end position and can be displaced in an opposite second rotational direction, wherein the dose metering member is coupled to the delivery device in such a way that the latter, when actuated, dispenses the product dose that has been selected by means of the dose metering member, the injection device also including an anti-twist safety device which has at least one anti-twist stop and at least one anti-twist counter-stop, one of which is formed by the housing and the other by the dose-metering member, wherein the anti-twist stop and the anti-twist counter-stop come to rest against one another in the end position in order to prevent the rotational displacement of the dose metering member in the first rotational direction from continuing beyond the end position.

27 Claims, 5 Drawing Sheets

U.S. PATENT DOCUMENTS

| | | | |
|---|---|---|---|
| 5,112,317 A | 5/1992 | Michel | |
| 5,226,895 A | 7/1993 | Harris | |
| 5,279,585 A | 1/1994 | Balkwill | |
| 5,295,976 A * | 3/1994 | Harris | 604/211 |
| 5,304,152 A | 4/1994 | Sams | |
| 5,383,865 A | 1/1995 | Michel | |
| 5,514,097 A | 5/1996 | Knauer | |
| 5,545,147 A * | 8/1996 | Harris | 604/209 |
| 5,584,815 A | 12/1996 | Pawelka et al. | |
| 5,591,136 A | 1/1997 | Gabriel | |
| 5,611,783 A | 3/1997 | Mikkelsen | |
| 5,630,796 A | 5/1997 | Bellhouse et al. | |
| 5,957,896 A | 9/1999 | Bendek et al. | |
| 6,146,361 A | 11/2000 | Dibiasi et al. | |
| 6,200,296 B1 * | 3/2001 | Dibiasi et al. | 604/272 |
| 6,221,046 B1 | 4/2001 | Burroughs et al. | |
| 6,235,004 B1 | 5/2001 | Steenfeldt-Jensen et al. | |
| 6,364,860 B1 * | 4/2002 | Steck et al. | 604/246 |
| 6,582,408 B1 | 6/2003 | Buch Rasmussen et al. | |
| 6,585,698 B1 * | 7/2003 | Packman et al. | 604/207 |
| 6,623,446 B1 | 9/2003 | Navelier et al. | |
| 6,899,698 B2 | 5/2005 | Sams | |
| 7,309,327 B2 * | 12/2007 | Kirchhofer et al. | 604/207 |
| 7,377,912 B2 | 5/2008 | Graf et al. | |
| 2004/0186431 A1 | 9/2004 | Graf | |
| 2004/0186441 A1 | 9/2004 | Graf | |
| 2004/0186442 A1 | 9/2004 | Graf | |
| 2004/0215152 A1 | 10/2004 | Kirchhofer et al. | |
| 2004/0215153 A1 | 10/2004 | Graf | |

FOREIGN PATENT DOCUMENTS

| | | |
|---|---|---|
| DE | 4425763 A1 | 1/1996 |
| EP | 0 058 536 B1 | 8/1982 |
| EP | 0498737 A1 | 8/1992 |
| EP | 0594349 A1 | 4/1994 |
| EP | 0 879 610 A2 | 11/1998 |
| EP | 0295075 A1 | 12/1998 |
| EP | 0 897 728 A1 | 2/1999 |
| EP | 1095668 A1 | 5/2001 |
| WO | 9717095 A1 | 5/1997 |
| WO | 9938554 A1 | 8/1999 |
| WO | 0002606 A1 | 1/2000 |

* cited by examiner

INJECTION APPARATUS WITH AN END POSITION-BLOCKED DOSAGE SETTING MEMBER

CROSS-REFERENCE TO RELATED APPLICATION(S)

This application is a continuation of International Application No. PCT/CH02/00684, filed Dec. 11, 2002, which claims priority to German Patent Application No. 202 09 051.5, filed on Jun. 6, 2002, and German Application No. 101 63 328.9, filed on Dec. 21, 2001, the contents of which are incorporated by reference in their entirety.

BACKGROUND

The invention relates to dosing in an injection apparatus for administering an injectable product in doses.

When administering products, in particular in medical applications, it is very important to dose the product precisely. In injection apparatus, the product is generally dosed with the aid of a dosing setting member which is coupled to a conveying means such that the dosage to be administered is selected with the aid of the dosing setting member and, when activated by the action of the conveying means, delivered. Through inappropriate handling, problems can arise from selecting the dosage. Problems which may be attributed to inappropriate handling occur to an increased extent in self-administering, as is for example common in the administering of insulin or growth hormone. Thus, a reaction movement by an element which is involved in dosing, caused by inappropriately performing dosing, can lead to incorrect dosing which is not noticed by the user.

An injection apparatus is known for example from EP 0 897 728 A1, in which the conveying means comprises a piston and a piston rod which acts on the piston and comprises a dosing thread. The piston rod is in threaded engagement with a dosing nut and in non-rotational engagement with a duplex dosage display sleeve for selecting the product dosage. The piston rod is mounted in a casing of the injection apparatus such that it can rotate about its longitudinal axis and move axially along the longitudinal axis. The dosing nut is mounted by the casing such that it can move axially along the rotational axis but cannot rotate about the rotational axis. A dosing rotational movement of the dosage display sleeve rotates the piston rod about its rotational axis and, due to the threaded engagement with the dosing nut in the casing, moves it axially in an advancing direction. The dosage display sleeve comprises two sleeve sections which can be rotated relative to each other, namely a sleeve section which displays the individual dosage units which can be selected and another sleeve section which displays the dosage units which can be selected in a division of ten. The two sleeve sections are connected non-rotationally to each other in discrete rotational positions with the aid of a split pin. The sleeve section with the division of ten can be rotated between two end positions, wherein in both end positions, a non-rotational connection to the sleeve section which displays the individual dosages exists due to the split pin. The non-rotational engagement between the piston rod and the dosage display sleeve is released when the piston rod assumes a front axial end position after performing a delivery stroke, and is re-established when the piston rod is returned to a rear axial end position. An unnoticed incorrect dosing can occur, for example, if the dosage display sleeve is situated in one of its end positions when the non-rotational engagement with the piston rod is established. The reason is that in order to establish the non-rotational connection, the engagement elements of the piston rod and the dosage display sleeve necessary for this have to "catch" each other, i.e., they are aligned with each other for the engagement.

SUMMARY

It is an object of the invention to reduce the danger of unnoticed incorrect dosing in injection apparatus.

In one embodiment, the present invention comprises an injection device comprising a housing with a reservoir for an injectable product, a delivery device for dispensing a product dose from the reservoir, a dose metering member which, in order to select the product dose, can carry out a rotational displacement in relation to the housing in a first direction until it reaches an end position and can be displaced in an opposite second rotational direction, wherein the dose metering member is coupled to the delivery device in such a way that the latter, when actuated, dispenses the product dose that has been selected by means of the dose metering member, and a safety device comprising at least one stop and at least one counter-stop, one of which is formed by the housing and the other by the dose-metering member, wherein the stop and the counter-stop abut or rest against one another in the end position to prevent the rotational displacement of the dose metering member in the first rotational direction.

In one embodiment, the present invention comprises an injection device comprising a housing with a reservoir for an injectable product, a delivery device used to dispense a product dose from the reservoir, and a dose metering member which, in order to select the product dose, can carry out a rotational displacement in relation to the housing in a first direction until it reaches an end position and can be displaced in an opposite second rotational direction, wherein the dose metering member is coupled to the delivery device in such a way that the latter, when actuated, dispenses the product dose that has been selected by means of the dose metering member, the injection device further comprising an anti-twist safety device which has at least one anti-twist stop and at least one anti-twist counter-stop, one of which is formed by the housing and the other by the dose-metering member, wherein the anti-twist stop and the anti-twist counter-stop come to rest against one another in the end position in order to prevent the rotational displacement of the dose metering member in the first rotational direction from continuing beyond the end position.

The subject of the invention is an injection apparatus which comprises a casing, a conveying means, a dosage setting member coupled to the conveying means and a rotational block. The casing itself can directly form a reservoir for an injectable product. Preferably, however, the casing forms a receptacle for a container which forms the reservoir, preferably an ampoule. A product dosage to be administered is selected with the aid of the dosage setting member.

The conveying means serves to deliver the selected product dosage by suitably acting on the product situated in the reservoir, for which it preferably forms a displacement pump. For selecting the product dosage, the dosage setting member can be rotationally moved relative to the casing in a first rotational direction and in a second rotational direction opposite to the first rotational direction. It is preferably mounted directly by the casing, such that it can move. This rotational movement, which in the following shall also be referred to as a dosing rotational movement, can be performed in the first rotational direction up to an end position. The conveying means and the dosage setting member are coupled to each other, preferably mechanically, such that the conveying means conveys the product dosage selected by means of the dosage setting member through an outlet of the reservoir, and in this sense delivers it, when the conveying means is activated. The conveying means can in principle be driven, for example by a motor or by means of a spring force, and only triggered manually, however the conveying means preferably does not comprise a drive of its own but rather the movement of the conveying means necessary for conveying is provided manually.

The rotational block comprises a rotational stopper and a rotational counter stopper, one of which is formed by the casing and the other by the dosage setting member. In the end position cited, the rotational stopper and the rotational counter stopper abut against each other in the first rotational direction, thus preventing a rotational movement of the dosage setting member beyond the end position in the first rotational direction. The block formed by the stoppers acts as a positive lock and cannot be overcome without destroying the parts forming the stoppers.

The dosage setting member is advantageously permanently in mechanical engagement with the conveying means, said engagement not being released during proper use of the injection apparatus.

In a preferred embodiment, the dosage setting member is formed in one piece or is formed from pieces which are connected to each other non-rotationally with respect to its dosing rotational movement.

In a preferred embodiment, the conveying means comprises a driven means which performs a delivery movement in an advancing direction along a translational axis, in order to deliver the selected product dosage, and a drive means which causes the delivery movement to be performed. The driven means and the drive means can be formed in one piece, but are more preferably formed by separate parts of the conveying means which are in mechanical engagement with each other. The dosage setting member is coupled to the driven means such that a dosing rotational movement which the dosage setting member and the driven means perform relative to each other about the translational axis causes a translational dosing movement of the dosage setting member along the translational axis relative to the driven means and the casing. Furthermore, the engagement is preferably configured such that the dosage setting member is slaved by the driven means during the delivery movement.

The driven means can comprise a piston which is provided with a dosing thread. In this embodiment, when the injection apparatus is assembled, a piston also forms a part of the conveying means, wherein said piston is arranged in the reservoir, seals the reservoir fluid-tight against the piston rod and is shifted along the translational axis towards an outlet of the reservoir during the delivery movement of the piston rod, such that the selected product dosage is delivered through the reservoir outlet. The dosage setting member preferably comprises a dosing counter thread which is in threaded engagement with the dosing thread of the piston rod, said threaded engagement forming the coupling between the conveying means and the dosage setting member.

The end position of the dosage setting member, blocked by the rotational block, can be a position which the dosage setting member assumes when a minimum dosage is selected, wherein the minimum dosage can be the zero dosage or in principle also a minimum dosage to be differentiated from the zero dosage. The end position can also, however, instead be a position which the dosage setting member assumes when the maximum selectable dosage, i.e., the maximum dosage, is selected. In a particularly preferred embodiment, the dosage setting member is blocked by the rotational block both against rotating beyond the end position corresponding to the minimum dosage and against rotating beyond the end position corresponding to the maximum dosage. Where the two end positions are to be differentiated in the following, the end position corresponding to the minimum selectable dosage is referred to as "minimum dosage stop" and the end position corresponding to the maximum selectable dosage is referred to as "maximum dosage stop".

If the rotational block blocks against rotating beyond both end positions, the rotational block forms at least one pair of stoppers, consisting of a rotational stopper and a rotational counter stopper, for each of the two end positions. The at least one rotational stopper and the at least one rotational counter stopper for one of the two end positions can be formed identically to the at least one rotational stopper and the at least one rotational counter stopper for the other of the two end positions. The pairs of stoppers can, however, also be formed differently, which can be advantageous for example if the geometrical relationships in the vicinity in which the respective pair of stoppers cooperate are different or possibly even necessitate a different formation.

A translational movement is preferably superimposed on the dosing rotational movement of the dosage setting member, such that the dosing movement of the dosage setting member is composed of a rotational and a translational movement component. If the conveying means comprises a piston rod with a dosing thread and the dosage setting member and the piston rod are in threaded engagement with each other, the piston rod in this embodiment is preferably connected to the casing such that it cannot rotate about its longitudinal axis but can move translationally back and forth along the longitudinal axis, while the dosage setting member can perform an exact dosing movement relative to the casing and the piston rod, consisting of a rotation and a superimposed translation. The longitudinal axis of the piston rod simultaneously forms the cited translational axis of the conveying means, the threaded axis of the threaded engagement and the rotational axis of the dosage setting member.

Although a rotational block which blocks the dosage setting member both in the "minimum dosage stop" position and in the "maximum dosage stop" position is already sufficient to limit the adjustment path of the dosage setting member between these two end positions, stoppers for the dosage setting member acting in both axial directions are preferably also additionally formed as well. In such an embodiment, there would exist—without the rotational block—the danger of the user, when selecting the dosage, pressing the dosage setting member against one of the axially acting stoppers—screwing the dosage setting member against the corresponding axial stopper, so to speak—with such a force that the piston rod as the reaction member is moved towards or away from the piston. From this, there arises the danger that a different dosage is selected than is displayed by a display of the injection apparatus. Due to the rotational block, however, this is prevented from the start.

If the dosing movement of the dosage setting member is a movement composed of a translation and a rotation, then a dosage setting member composed of one piece or of pieces connected non-rotationally to each other can advantageously perform more than one revolution about its rotational axis over its maximum possible adjustment path. In this way, selecting the dosage per delivery can be refined or the selectable dosage per delivery can be increased, as compared to an adjustment path comprising only one revolution or less.

A number of rotational stoppers and/or a number of rotational counter stoppers are preferably formed in uniform distribution about the rotational axis of the dosing rotational movement of the dosage setting member. In principle, it would be sufficient to form a single rotational stopper and a single rotational counter stopper for the block in the end position, or one such pair of stoppers for each blocked end position.

In one advantageous embodiment, an elastically flexible latch forms the rotational stopper or one elastically flexible latch forms each of a number of rotational stoppers. The at least one latch is particularly advantageously formed as an elastically bending tongue. Although it would in principle be possible for the tongue to elastically bend in one of the rotational directions of the dosage setting member or in both rotational directions, a tongue which is not flexible in any of the rotational directions is preferred. The tongue should be flexible in a direction which has a radial direction component with respect to the rotational axis of the dosing rotational movement, or more preferably still, points radially with respect to the rotational axis. Such a latch, formed as a tongue, preferably projects tangentially, i.e., in one of the rotational directions of the dosage setting member, from the dosage setting member or the casing. Furthermore, it should be curved towards the rotational axis of the dosing rotational movement, preferably with a constant radius of curvature of its radial distance from the rotational axis. The latch forms the at least one rotational stopper as a stopper area pointing in the first rotational direction, preferably at a front, free latch end with respect to the first rotational direction. The latch can also be elastically flexible in the axial direction. Preferably, however, it is not flexible in the axial direction, at least not under the axial forces occurring during operation.

The casing and the dosage setting member preferably surround each other, at least in an axial section of each, preferably in a sleeve section of each, wherein the at least one rotational stopper and the at least one rotational counter stopper are formed in said section of the casing and said section of the dosage setting member. If the at least one rotational stopper is formed by an elastic latch, then the latch supported on a first section of said sections is elastically tensed against the other, second section of said sections. The at least one rotational counter stopper protrudes from the second section towards the first section and is preferably rigid, i.e., not flexible. The rotational counter stopper can also be formed by a side wall of a receptacle in the second section, into which the elastically tensed latch can pre-latch, such that when it reaches the blocked end position in the first rotational direction, it comes to rest against the side wall of the receptacle in question.

While the preferred embodiment for forming the at least one rotational stopper and the at least one rotational counter stopper as an elastic latch on the one hand and a rigid counter stopper on the other has been emphasized above, both the rotational stopper and the rotational counter stopper can also each be formed as an elastic latch or as a rigid stopper. If, however, at least one of the two functional parts is flexible, then an obstruction in the non-blocked rotational direction can be easily avoided. The formation as an elastically bending latch which is rigid in the rotational direction is particularly preferable, since in this case, the cited advantage is also added to the advantage of the rigid and therefore secure block. It is also possible to form the at least one rotational stopper and the at least one rotational counter stopper to be rigid with respect to the blocked rotational direction. When forming the rotational block in this way, it is preferable if the at least one rotational stopper and the at least one rotational counter stopper protrude towards each other in and counter to the advancing direction.

In some embodiments, the injection apparatus can be an injection pen, preferably a semi-disposable pen. In such semi-disposable pens, a reservoir module designed as a disposable module and a reusable dosing and activating module, when combined, form the injection apparatus. When combining these two modules, the dosage setting member is connected to a dosing and activating element of the dosing and activating module. In such semi-disposable pens, the rotational block in accordance with the invention advantageously prevents the possibility of torque, which could trigger reaction movements, being exerted on the conveying means when establishing the connection.

BRIEF DESCRIPTION OF THE DRAWINGS

Exemplary embodiments of the invention are explained below with reference to the following figures.

DETAILED DESCRIPTION

Figure 1:
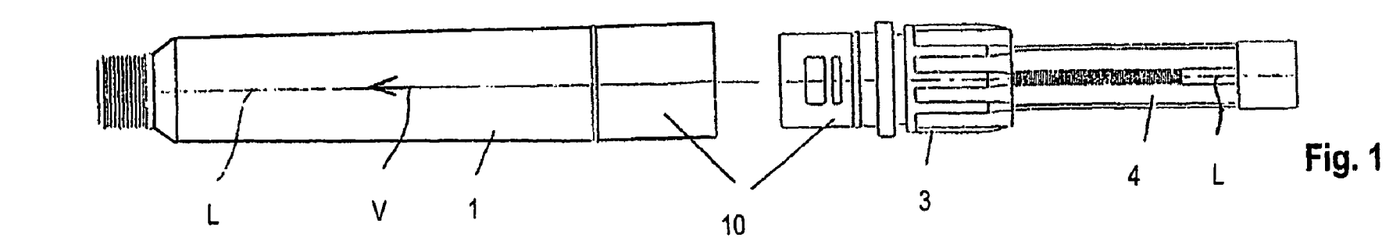
FIG. 1 depicts two parts of a reservoir module of an injection apparatus.

FIG. 1 shows a view of a reservoir part 1 and a mechanism holder 3 which are connected to each other to form a reservoir module 10 of an injection apparatus. The reservoir part 1 is essentially a hollow cylinder which has a circular cross-section and comprises a connecting region at its front end for a connection to a needle holder for an injection needle, such as a 31-gauge injection needle. The reservoir part 1 serves to accommodate a reservoir container which is preferably formed by an ampoule. The reservoir container is filled with an injectable product, for example insulin or a growth hormone. An outlet at the front end of the reservoir container is sealed fluid-tight by a membrane. When the needle holder is fixed to the front end of the reservoir part 1, a rear part of the injection needle pierces the membrane, such that a fluid connection is established between the tip of the injection needle and the reservoir. A rear end of the reservoir container axially opposite the outlet is sealed fluid-tight by a piston which can be shifted along a longitudinal axis L towards the outlet of the reservoir container, in order to displace product from the reservoir container. In FIG. 1, a piston rod 4 can be seen which protrudes into the mechanism holder 3 at a rear end of the mechanism holder 3 facing away from the reservoir part 1 and is mounted by the mechanism holder 3 such that it can be moved in an advancing direction V pointing along the longitudinal axis L towards the reservoir outlet.

Figure 2:
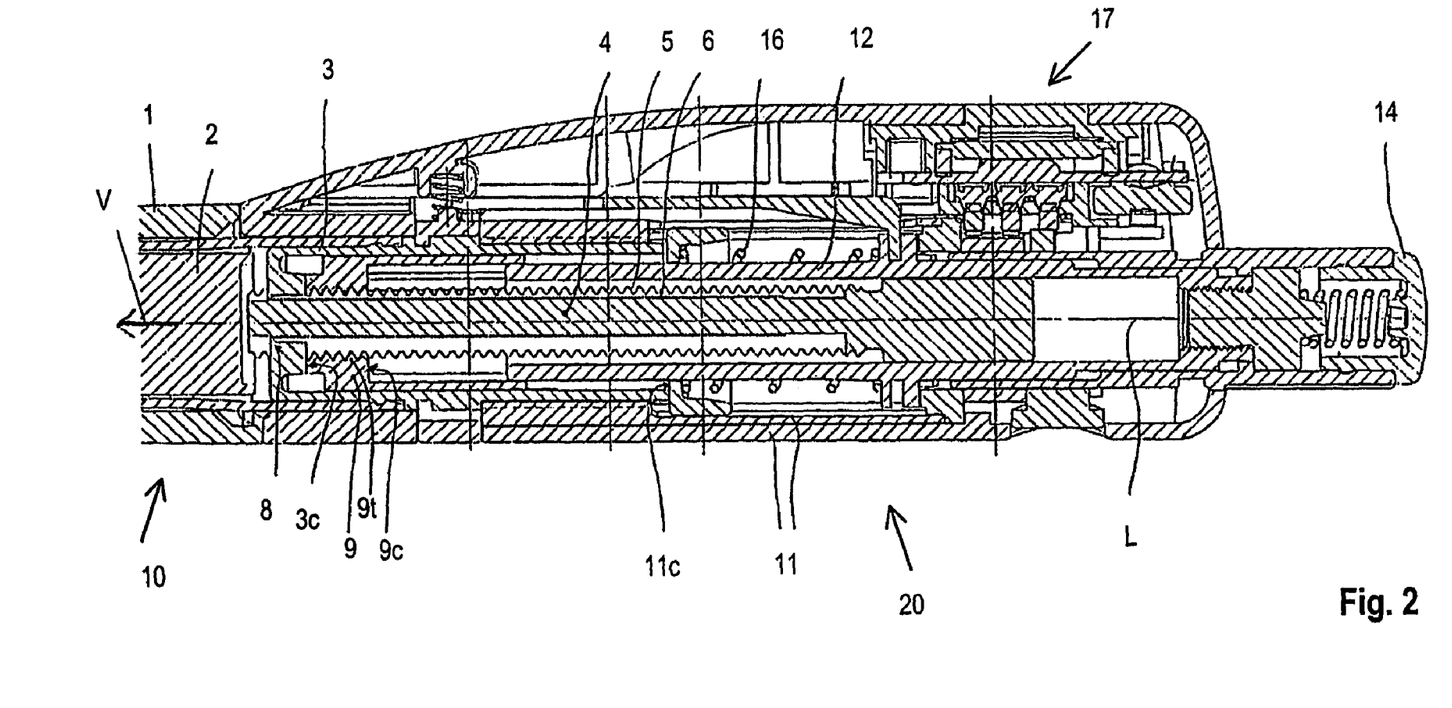
FIG. 2 depicts the injection apparatus in a longitudinal section.
Figures 3, 4:
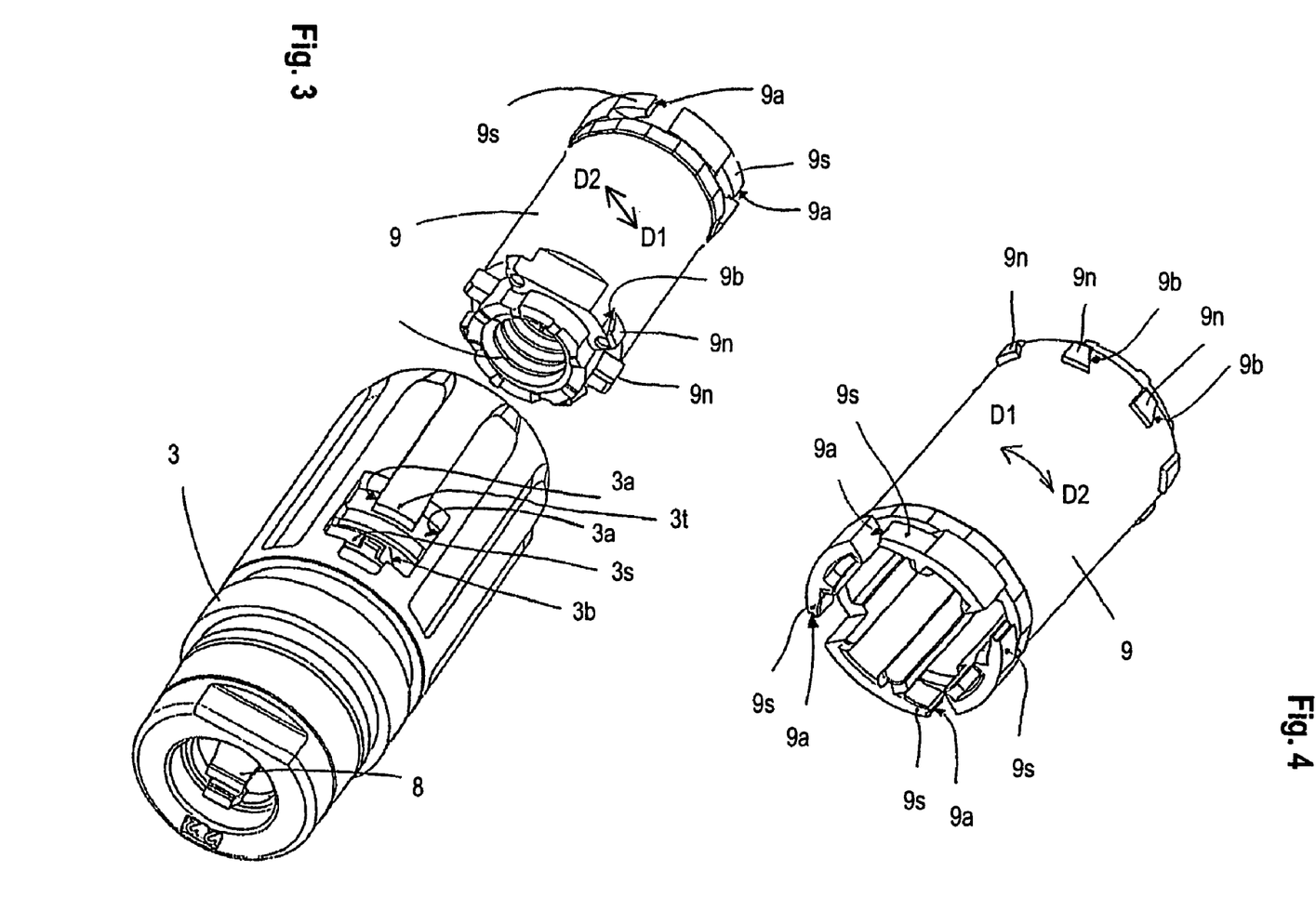
FIG. 3 depicts dosage setting member and a sleeve body of a casing of the injection apparatus in a perspective representation, in accordance with one embodiment.
FIG. 4 depicts the dosage setting member in another perspective representation.

FIG. 2 shows a rear part of the injection apparatus in a longitudinal section. The injection apparatus is formed by the reservoir module 10 and a dosing and activating module 20. The rear end of the reservoir module 10 can be seen in FIG. 1. The reservoir container is completely filled with product, such that the rear part of the piston 2 can only just still be seen. The piston rod 4 advances the piston 2 in the advancing direction V towards the reservoir outlet, wherein it presses against the piston 2 with its front end. The longitudinal axis L is the translational axis of the piston 2 and the piston rod 4. The piston rod 4 is held by the mechanism holder 3, such that it can be moved in the advancing direction V once a certain resistance has been overcome, but cannot be moved counter to the advancing direction V. The piston rod 4 is prevented from moving backwards counter to the advancing direction V by a blocking means 8. Two elastic locking tongues, protruding radially towards each other, form the blocking means 8. The piston rod comprises two axially extending rows of serrated teeth 6 opposite the locking tongues, said locking tongues of the blocking means 8 engaging with said serrated teeth 6. The serrated teeth 6 are sloped in the advancing direction V in order to permit the translational movement of the piston rod 4 in the advancing direction V. Their rear ends, however, are shaped such that movement backwards is prevented by the engagement of the locking tongues 8.

A dosage setting member 9 is also accommodated in the mechanism holder 3. The dosage setting member 9 is formed as a threaded nut and is in threaded engagement via its inner thread 9t with a dosing thread 5 of the piston rod 4. The piston rod 4 is linearly guided in the advancing direction V, non-rotational with respect to the longitudinal axis L, by the mechanism holder 3. The dosage setting member 9 is also axially guided by the mechanism holder 3, however the dosage setting member 9 can perform a rotational movement about the longitudinal axis L relative to the mechanism holder 3 and the piston rod 4. The piston rod 4 and the dosage setting member 9 form a spindle drive, for selecting the product dosage to be administered.

The reservoir part 1 and the mechanism holder 3 are non-rotationally and non-shiftably connected to each other and together form the reservoir module 10 of the injection apparatus. The reservoir module 10 therefore also comprises the piston rod 4 held by means of the blocking means 8 and the dosage setting member 9. The reservoir part 1 and the mechanism holder 3 together form a front casing section of the injection apparatus. A rear casing section 11 is non-rotationally and non-shiftably connected to said front casing section. The rear casing section 11 forms the support of a dosing and activating element 12 and—together with the latter and a display means 17 and other parts of the injection apparatus— the dosing and activating module 20.

A dosing and activating device of the injection apparatus comprises—except for the dosage setting member 9 and the piston rod 4—the other components for selecting the product dosage and activating the injection apparatus. In particular, it comprises the dosing and activating element 12 and the counting and display means 17 for counting and optically displaying the selected product dosage. Not least because of the counting and display means 17, the dosing and activating module 20 is a high-quality and therefore expensive part of the injection apparatus. While the comparatively inexpensive reservoir module 10 is designed as a disposable module, which is disposed of or reprocessed by a manufacturer once the reservoir has been emptied, the dosing and activating module 20 is intended for repeated use, with constantly new reservoir modules 10.

For selecting the product dosage, the dosing and activating element 12 is mounted by the rear casing section 11 such that it can be rotated about the longitudinal axis L and also linearly shifted along the longitudinal axis L, in and counter to the advancing direction. The dosing and activating element 12 is hollow cylindrical and surrounds the piston rod 4 via a front section. It also protrudes into the sleeve-shaped dosage setting member 9 via its front section. A rear section of the dosing and activating element 12 protrudes out beyond a rear end of the casing section 11 and is sealed by a cap 14.

A restoring spring 16 elastically tenses the dosing and activating element 12 counter to the advancing direction V, into the rear axial position shown in FIG. 2, which is referred to in the following as the initial position. In the initial position, the dosage can be selected by rotating the dosing and activating element 12 about the longitudinal axis L. Then, also from the initial position, the selected product dosage can be delivered by axially shifting the dosing and activating element 12 in the advancing direction V.

The dosage setting member 9 and the dosing and activating element 12 are axially and linearly guided on each other and connected to each other such that they cannot rotate about the longitudinal axis L. In the event of a rotational movement of the dosing and activating element 12, the dosage setting member 9—due to the non-rotational connection to the dosing and activating element 12 on the one hand and the threaded engagement with the piston rod 4, which is held by the blocking means 8 and cannot rotate relative to the mechanism holder 3, on the other—is set into a movement composed of a rotational movement component about the longitudinal axis L and a translational movement component along the longitudinal axis L. This movement is referred to in the following as the dosing rotational movement of the dosage setting member 9. The dosing rotational movement is limited by a rotational block, such that the dosage setting member 9 can be moved in a first rotational direction up to a front, first end position and in an opposite, second rotational direction up to a rear, second end position. The rotational block prevents the dosage setting member 9 from being able to move beyond the two end positions relative to the mechanism holder 3. When the dosage setting member 9 assumes its first end position, the minimum selectable dosage—in the example embodiment, the zero dosage—is set. When the dosage setting member 9 assumes the second end position, the maximum selectable dosage is set. The first end position is referred to in the following as the "minimum dosage stop" and the second end position as the "maximum dosage stop".

Via a rear abutting area, the dosage setting member 9 forms a translational stopper 9c for the dosing and activating element 12. A translational movement of the dosing and activating element 12 relative to the dosage setting member 9 in the advancing direction V is only possible up until the dosing and activating element 12 comes to rest against the stopper 9c. As soon as there is contact on the stopper 9c, the dosing and activating element 12 slaves the dosage setting member 9 in a continuing movement in the advancing direction V, up to the front end position, which is defined by a translational stopper 3c of the mechanism holder 3. The dosage setting member 9 in turn slaves the piston rod 4 due to the threaded engagement.

Proceeding from the initial state of the injection apparatus shown in FIG. 2, the dosage is selected and the product delivered. The dosing and activating element 12 assumes its initial position, i.e., its rearmost axial position, and the dosage setting member 9 assumes the "minimum dosage stop" position. In the "minimum dosage stop" position, the dosage setting member 9 is prevented from moving in the advancing direction V, on the one hand by the rotational block and on the other by the translational stopper 3c formed by the mechanism holder 3. The stopper 3c serves to block the purely axial movement which the dosage setting member 9 and the piston rod 4 perform jointly during a delivery stroke, while the rotational block prevents the dosage setting member 9 from rotating relative to the piston rod 4 in a first rotational direction leading beyond the "minimum dosage stop" position.

In order to select the dosage to be administered, the dosing and activating element 12 is rotated about the longitudinal axis L. Due to the non-rotational connection, the dosing and activating element 12 slaves the dosage setting member 9 as it rotates. Due to the threaded engagement with the piston rod 4, this dosing rotational movement of the dosage setting member 9 in the second rotational direction, opposite to the first rotational direction, leads to a translational movement of the dosage setting member 9 along the longitudinal axis L, counter to the advancing direction V. The dosage setting member 9 performs the translational movement not only relative to the mechanism holder 3 but also relative to the dosing and activating element 12. This reduces a slight distance between the stopper 9c formed by the dosage setting member 9 and a counter stopper formed by the dosing and activating element 12; in the example embodiment, the free front end of the dosing and activating element 12. In the course of this dosing rotational movement of the dosage setting member 9, the axial and angular position of the dosage setting member 9 corresponds respectively to the product dosage which would be delivered if the dosing and activating element 12 were activated. The counting and display means 17 displays this product dosage.

Once the product dosage has been selected, the selected product dosage can be delivered by activating the dosing and activating element 12. The dosing and activating element 12 is activated by pressing it in the advancing direction V. The dosing and activating element 12 thus travels a first part of its path length alone, until it comes to rest against the translational stopper 9c of the dosage setting member 9. In the course of its subsequent axial movement, it then slaves the dosage setting member 9 and the piston rod 4, until the dosage setting member 9 abuts against the translational stopper 3c formed by the mechanism holder 3. At this moment, the delivery stroke is complete. If the dosing and activating element 12 is released, then it slides back to its initial position shown in FIG. 2 due to the elasticity force of the restoring spring 16 which presses counter to the advancing direction V, while the piston rod 4 and the dosage setting member 9 maintain the new axial position which they have just assumed due to the locking action of the blocking means 8. Performing the delivery stroke or restoring the piston rod 4 re-sets the counting and display means 17 back to the minimum dosage, in the exemplary embodiment zeroing it. In the initial position which the dosing and activating element 12 has reached again, the product dosage for the next delivery can be selected. While the injection apparatus is assembled, the mechanical engagement between the dosage setting member 9 and the piston rod 4 on the one hand and the dosage setting member 9 and the dosing and activating element 12 on the other is not released in any phase of the progression of movement.

FIGS. 3 to 8 show the mechanism holder 3 and the dosage setting member 9 and in particular the rotational block formed by these parts. The mechanism holder 3 and the dosage setting member 9 are each sleeve bodies composed of one piece, wherein—as can be seen in FIG. 2—the mechanism holder 3 surrounds the dosage setting member 9 concentrically with respect to the longitudinal axis L.

The rotational block is formed by pairs of stoppers consisting of rotational stoppers and rotational counter stoppers for the "minimum dosage stop" position and by other pairs of stoppers consisting of rotational stoppers and rotational counter stoppers for the "maximum dosage stop" position. The block with respect to the "minimum dosage stop" position is formed by rotational stoppers 9a of the dosage setting member 9 and rotational counter stoppers 3a of the mechanism holder 3. Rotational stoppers 3b of the mechanism holder 3 and rotational counter stoppers 9b of the dosage setting member 9 form the block for the "maximum dosage stop" position. The two rotational directions D1 and D2 of the dosage setting member 9 are also each indicated by a direction arrow.

The rotational stoppers 9a are stopper areas which operate in the first rotational direction D1 by pointing in the first rotational direction D1. Each rotational stopper 9a is formed by a latch 9s. A number of latches 9s are formed on a rear end of the dosage setting member 9, in uniform distribution on its outer circumference. Each of the latches 9s is formed as an elastically bending tongue which projects, curved in the first rotational direction D1 about the longitudinal axis L, freely from a surface segment of the dosage setting member 9, and each forms a stopper area 9a on its front free end with respect to the first rotational direction D1. The latches 9s protrude in the radial direction slightly beyond the rest of the dosage setting member 9 via their free ends. Each of the latches 9s can be elastically bent towards the longitudinal axis L and can thus be regarded as a bending beam extending from its foot end—the point of fixed clamping—to its free end forming the stopper area 9a.

The mechanism holder 3 forms the rotational counter stoppers 3a cooperating with the rotational stoppers 9a through side walls which oppose and face the rotational stoppers 9a when the dosage setting member 9 is rotated in the first rotational direction D1. The rotational counter stoppers 3a could alternatively be formed by protrusions which in such an alternative embodiment would protrude inwards towards the longitudinal axis L beyond an otherwise circular cylindrical inner surface area of the mechanism holder 3. The mechanism holder 3 forms a total of four rotational counter stoppers 3a. In the sleeve surface of the mechanism holder 3, which when assembled surrounds the dosage setting member 9, a window is relieved on each of the diametrically opposing sides with respect to the longitudinal axis L. Two of the four rotational counter stoppers 3a are arranged in each of the two window regions. A side wall of the window in question forms one of the rotational counter stoppers 3a, the other in each case is formed by a rib 3r protruding into the window in the axial direction. The rotational counter stoppers 3a formed in this way are the plane counter stopper areas on the side wall and the rib 3r, opposing and facing the rotational stoppers 9a counter to the first rotational direction D1, and each lying in an axial/radial plane with respect to the longitudinal axis L. The rotational counter stoppers 3a are rigid, i.e., not flexible.

For the part of the rotational block which blocks the dosage setting member 9 in the "maximum dosage stop" position, the mechanism holder 3 forms the rotational stoppers 3b on two elastic latches 3s. Each of the latches 3s is arranged in one of the windows relieved from the mechanism holder 3. The latches 3s are also each formed by an elastically bending tongue which freely protrudes from a side wall of its window. For each of the latches 3s, as already for the latches 9s, the stopper area formed on the respectively free latch end is understood as the rotational counter stopper 3b. Since the latches 3s are formed on the mechanism holder 3, their stopper areas 3b also point in the first rotational direction D1. The two stopper areas 3b each form a plane which points obliquely with respect to an axial/radial plane with respect to the longitudinal axis L. A cam which protrudes radially outwards is formed on each of the latches 3s and serves to elastically press its latch 3s slightly inwards when the injection apparatus is assembled (FIG. 2). Without this pressure, i.e., before the reservoir module 10 and the dosing and activating module 12 are assembled, the rotational stoppers 3b are free of the rotational counter stoppers 9b.

The rotational counter stoppers 9b which cooperate with the rotational stoppers 3b are formed, non-flexible, on the dosage setting member 9. Each rotational counter stopper 9b is formed by a cam 9n. The cams 9n are formed at a front end of the dosage setting member 9, in uniform distribution over the circumference on a surface outer area, and protrude radially outwards. The cams 9n form the rotational counter stoppers 9b, each as a counter stopper area 9b pointing in the second rotational direction D2. The rotational counter stoppers 9b each point, at the same angle of inclination as the stopper areas 3b, obliquely with respect to an axial/radial plane with respect to the longitudinal axis L. The rotational counter stoppers and/or stopper areas 3b and the rotational stoppers and/or counter stopper areas 9b cooperate in the manner of inclined planes when the dosage setting member 9 is moved in the second rotational direction D2 into the "maximum dosage stop" position.

The rotational block can block the dosage setting member 9 in a number of rotational angular positions, wherein the number of said rotational angular positions corresponds to the number of dosages which can be discretely set over a rotational angle of 360°. This ensures that the dosage setting member 9 can be further rotated beyond the blocked end positions by at most one settable dosage unit in each case. The pairs of stoppers 9a and 3a for the "minimum dosage stop" position and the pairs of stoppers 3b and 9b for the "maximum dosage stop" position are arranged, adjusted to the locking positions which the dosage setting member 9 can assume relative to the mechanism holder 3 when selecting the dosage. The adjustment is such that in each of its locking positions, the dosage setting member 9 can perform the delivery movement up to the translational stopper 3c of the mechanism holder 3, unimpeded by the rotational block.

Figure 5:
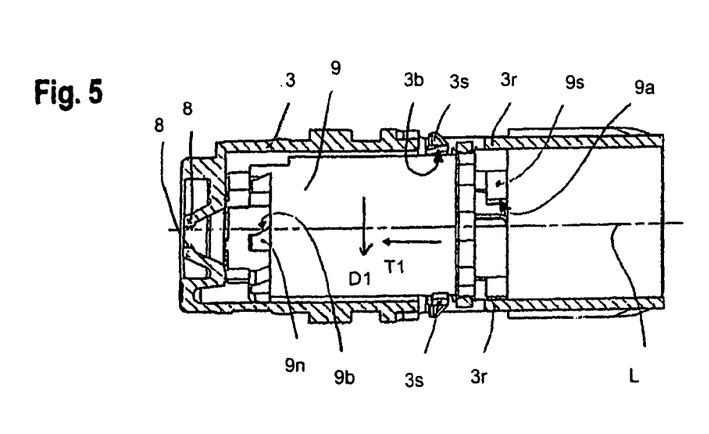
FIG. 5 depicts the sleeve body and the dosage setting member in a blocked end position of the dosage setting member, in a longitudinal section.
Figure 6:
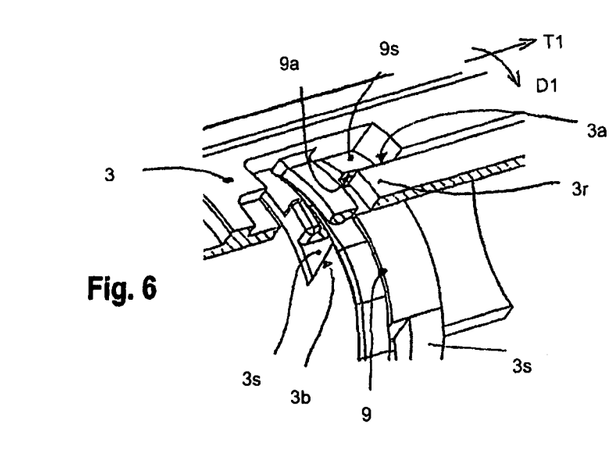
FIG. 6 is a perspective view onto a part of a rotational block blocking the dosage setting member in the end position in FIG. 5.

FIGS. 5 and 6 show the mechanism holder 3 and the dosage setting member 9 in the "minimum dosage stop" position of the dosage setting member 9. The first rotational direction D1 leading into this position is again indicated by direction arrows, and also the direction T1 of the resultant translational movement of the dosage setting member 9. FIG. 6 shows an abutting pair for this position, consisting of one of the rotational stoppers 9a and one of the rotational counter stoppers 3a.

Figure 7:
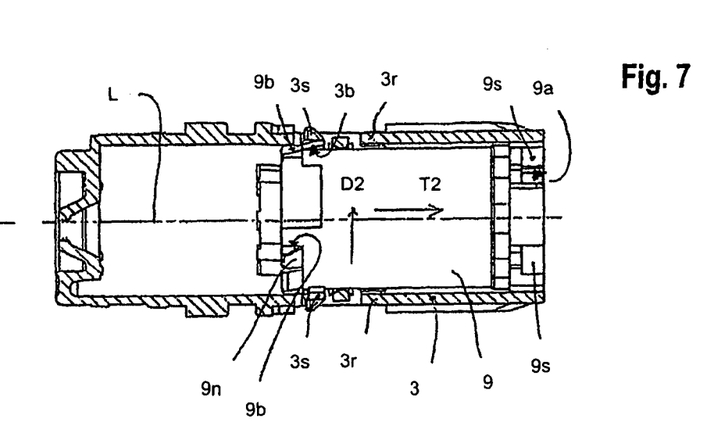
FIG. 7 depicts the sleeve body and the dosage setting member, directly before reaching a blocked other end position of the dosage setting member, in a longitudinal section.
Figure 8:
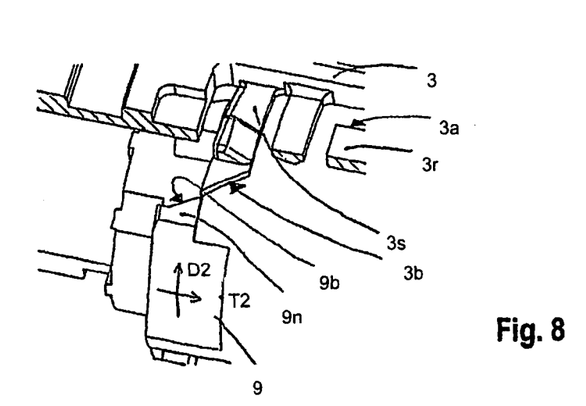
FIG. 8 is a perspective view onto a part of the rotational block blocking the dosage setting member in the other end position.
Figure 9:
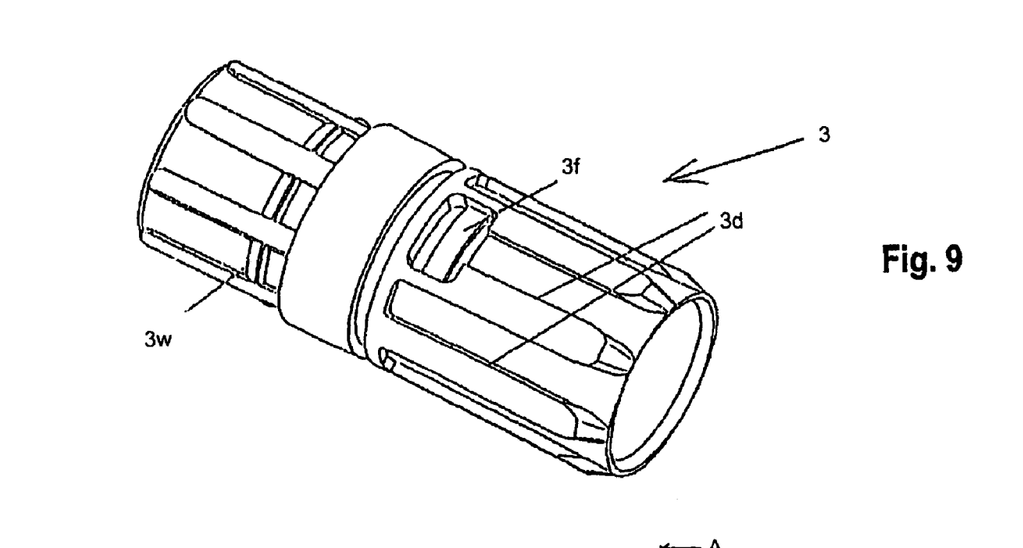
FIG. 9 is a perspective representation of a sleeve body of the casing, in accordance with another embodiment.
Figure 10:
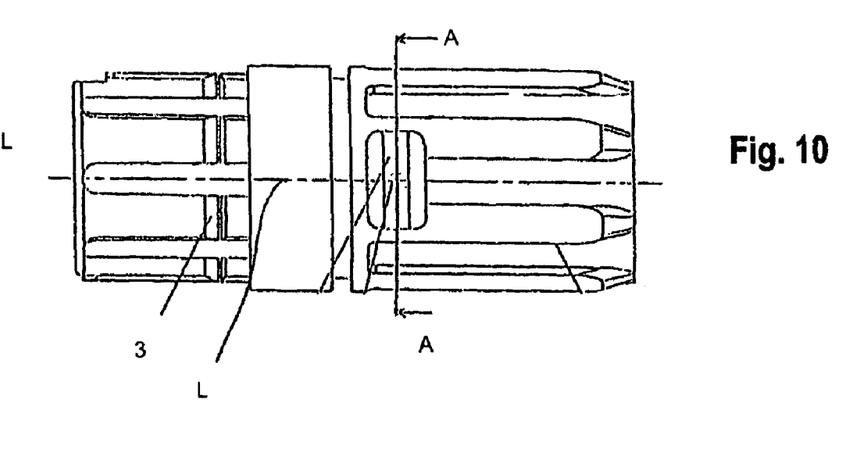
FIG. 10 depicts the sleeve body of FIG. 9 in a side view.
Figure 11:
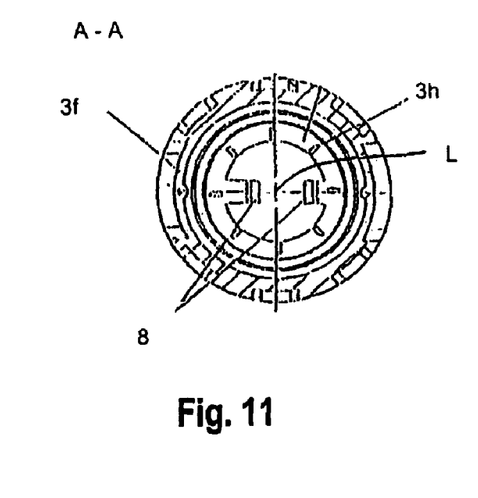
FIG. 11 is the sleeve body of FIG. 9 in a frontal view.
Figure 12:
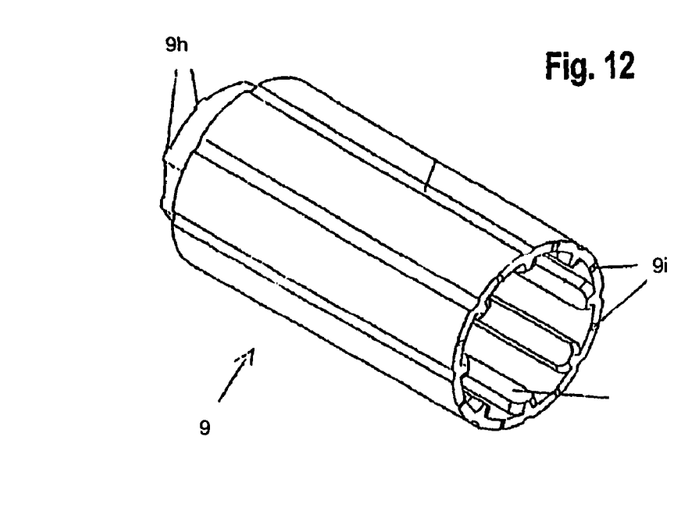
FIG. 12 is a perspective representation of a dosage setting member in accordance with the embodiment of FIG. 9.
Figure 13:
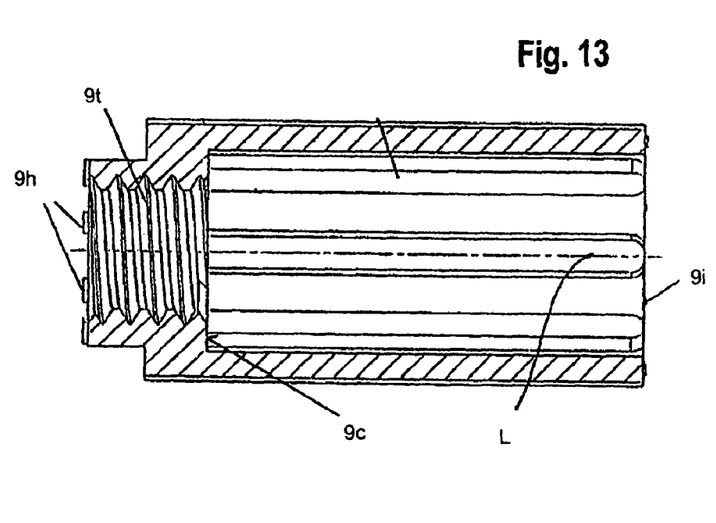
FIG. 13 depicts the dosage setting member of FIG. 9 in a longitudinal section.
Figure 14:
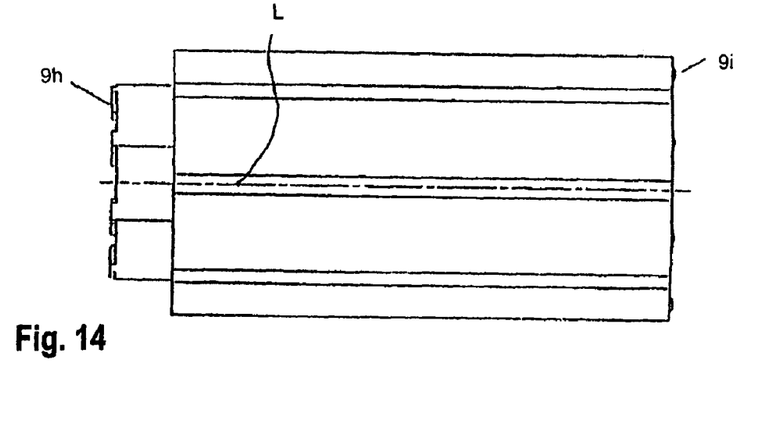
FIG. 14 depicts the dosage setting member of FIG. 9 in a side view.
Figure 15:
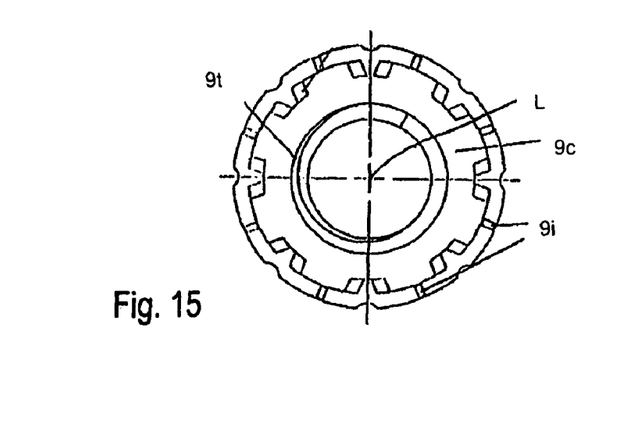
FIG. 15 depicts the dosage setting member of FIG. 9 in a frontal view.

FIGS. 7 and 8 show the mechanism holder 3 and the dosage setting member 9 in the extreme "maximum dosage stop" position of the dosage setting member 9. The second rotational direction D2, which leads into this end position, is again indicated as the direction arrow D2. The direction T2 of the superimposed translational movement is also indicated. FIG. 8 shows in particular how, due to the inclination of the stopper areas 3b and 9b, the pairs of stoppers "catch" each other when they reach the "maximum dosage stop" position, in order to then slide off of each other in the manner of inclined planes. This brief sliding movement is terminated either by self-locking or by an axially extending rear end of the counter stopper area 9b with respect to the direction T2 of the translational movement, i.e., the counter stopper area 9b kinks towards the longitudinal axis L.

The latches 9s and the latches 3s elastically flex radially inwards during the rotational movement of the dosage setting member 9 which leads out of the end position which they respectively block, if they graze over their rotational counter stoppers 3a and 9b during the rotational movement, such that the dosing rotational movement between the "minimum dosage stop" end position and the "maximum dosage stop" end position is not obstructed.

FIGS. 9 to 15 show a mechanism holder 3 and a dosage setting member 9 which form a rotational block for blocking the "minimum dosage stop" end position and the "maximum dosage stop" end position, in accordance with a second example embodiment. In the second example embodiment, the rotational stoppers and the rotational counter stoppers for both end positions are formed by non-flexible protrusions which protrude towards each other. For blocking the "minimum dosage stop" position, the rotational stoppers 9h of the dosage setting member 9 cooperate with the rotational counter stoppers 3h of the mechanism holder 3. For blocking the "maximum dosage stop" position, the rotational stoppers 9i of the dosage setting member 9 cooperate with the rotational counter stoppers of the rear casing section 11 (not shown). The rotational stoppers 9h project from a front abutting area of the dosage setting member 9, in the advancing direction V. The rotational stoppers 9i project from a rear abutting area of the dosage setting member 9, counter to the advancing direction V. Correspondingly, the rotational counter stoppers 3h project from the abutting area of the mechanism holder 3 which forms the translational stopper 3c for the delivery stroke, counter to the rotational stoppers 9h. The rotational counter stoppers for the rotational stoppers 9i project from a collar, protruding radially inwards, of the rear casing section 11, in the advancing direction V, counter to the rotational stoppers 9i. With respect to additional details of the rotational block of the second example embodiment and the additional formation of the mechanism holder 3 and the dosage setting member 9, reference is made to German patent application No. 101 63 328.9, which is hereby incorporated in this respect.

In the foregoing description, embodiments of the present invention, including preferred embodiments, have been presented for the purpose of illustration and description. They are not intended to be exhaustive or to limit the invention to the precise forms disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection apparatus with an end position-blocked dosing setting member, said injection apparatus comprising:
   a) a casing;
   b) a conveying means for delivering a selected product dosage;

c) a dosage setting member which rotates in order to select said product dosage and can perform a rotational movement in a first rotational direction to an end position and in an opposite, second rotational direction relative to said casing, said dosage setting member coupled to said conveying means such that when activated, the conveying means delivers the product dosage selected by said dosage setting member;

d) a dosing and activating element that can be rotated about and linearly shifted along a longitudinal axis, wherein the dosing and activating element extends beyond the casing and comprises a cylindrical section surrounding at least part of the conveying means, and wherein the dosing and activating element protrudes into the dosage setting member;

e) and a rotational block which comprises at least one rotational stopper and at least one rotational counter stopper one of which is associated with the casing and the other is formed by the dosage setting member;

f) wherein said rotational stopper and said rotational counter stopper abut against each other in the end position in said first rotational direction to prevent the dosage setting member from rotating in the first rotational direction beyond the end position.

2. The injection apparatus as set forth in claim 1, wherein the dosage setting member can be moved back and forth along a rotational axis of its rotational movement between the end position and another end position, relative to the casing.

3. The injection apparatus as set forth in claim 1, wherein the dosage setting member is formed in one piece or is formed from pieces which are permanently connected to each other non-rotationally with respect to the rotational movement.

4. The injection apparatus as set forth in claim 1, wherein the conveying means comprises a piston rod which can be moved in an advancing direction along a rotational axis of the rotational movement of the dosage setting member in order to perform a delivery stroke, and comprises a dosing thread about said rotational axis, and wherein the dosage setting member comprises a dosing counter thread which is in threaded engagement with said piston rod in order to select the product dosage.

5. The injection apparatus as set forth in claim 1, wherein a latch, which is elastically flexible in a direction which points radially with respect to a rotational axis of the rotational movement of the dosage setting member or at least has a radial direction component, forms the rotational stopper.

6. The injection apparatus as set forth in claim 5, wherein said latch is a tongue which elastically bends radially with respect to said rotational axis and which projects from the casing or the dosage setting member.

7. The injection apparatus as set forth in claim 5, wherein the latch extends at least substantially tangentially with respect to the rotational axis.

8. The injection apparatus as set forth in claim 7, wherein said latch extends in the circumferential direction with respect to the rotational axis.

9. The injection apparatus as set forth in claim 1, wherein a sleeve-shaped section of the casing and a cylindrical section of the dosage setting member surround each other about the rotational axis.

10. The injection apparatus as set forth in claim 9, wherein an elastic latch forming the rotational stopper is formed on one of said sleeve-shaped section of the casing or cylindrical section of the dosage setting member and is elastically tensed against the other of said sleeve-shaped section or cylindrical section in a direction which points radially with respect to a rotational axis of the rotational movement of the dosage setting member or has a radial direction component.

11. The injection apparatus as set forth in claim 10, wherein the rotational counter stopper comprises a protrusion extending from at least one of the sleeve-shaped or cylindrical sections toward the other of the sleeve-shaped or cylindrical section.

12. The injection apparatus as set forth in claim 1, wherein the rotational counter stopper is rigid.

13. The injection apparatus as set forth in claim 1, wherein the rotational stopper is formed in one piece with the dosage setting member and the rotational counter stopper is formed in one piece with the casing or the rotational stopper is formed in one piece with the casing and the rotational counter stopper is formed in one piece with the dosage setting member.

14. The injection apparatus as set forth in claim 1, wherein the rotational stopper and the rotational counter stopper are formed by stopper areas which extend at least substantially parallel to a rotational axis of the rotational movement of the dosage setting member.

15. The injection apparatus as set forth in claim 1, wherein the rotational stopper and the rotational counter stopper are formed by stopper areas which slide off of each other in the manner of inclined planes, up to the end position.

16. The injection apparatus as set forth in claim 1, wherein the injection apparatus comprises a 31-gauge injection needle.

17. An injection apparatus comprising:
a front casing section comprising a reservoir for an injectable product and a rear casing section;
means for conveying a selected product dosage from said reservoir;
a dosage setting member that rotates for selecting a product dosage, said dosage setting member rotationally moveable in a first rotational direction to an end position and in an opposite, second rotational direction relative to said front casing section, and coupled to said means for conveying such that when activated, the means for conveying delivers the product dosage selected;
a dosing and activating element that can be rotated about a longitudinal axis and linearly shifted along the longitudinal axis, in and counter to an advancing direction, wherein a portion of the dosing and activating element is a hollow cylinder that surrounds the conveying means, which protrudes beyond the rear casing section, wherein a section of the dosing and activating element protrudes into the dosage setting member, and wherein the rear casing section is non-rotationally and non-shiftably connected to the front casing section; and
a rotational block comprising at least one rotational stopper and at least one rotational counter stopper one of which is formed by the dosage setting member, wherein said rotational stopper and said rotational counter stopper abut each other in the end position to prevent the dosage setting member from rotating in the first rotational direction beyond the end position.

18. The injection apparatus according to claim 17, wherein the rotational stopper comprises a latch elastically and generally radially flexible with respect to a rotational axis of the dosage setting member.

19. The injection apparatus according to claim 17, wherein the front casing section has a generally sleeve-shaped section and the dosage setting member has a generally cylindrical section, wherein said sleeve-shaped or cylindrical sections are generally concentric about said rotational axis of the dosage setting member.

20. The injection apparatus according to claim 19, wherein an elastic latch forming the rotational stopper is formed on one of said sleeve-shaped or cylindrical sections and is elastically tensed against the other sleeve-shaped or cylindrical section in a generally radial direction with respect to said rotational axis of the dosage setting member.

21. An injection device comprising:
a front housing section and a rear housing section;
a delivery device for dispensing a product dose from a reservoir;
a dose metering member, which rotates in order to select the product dose, and can carry out a rotational displacement in relation to the front housing section in a first direction until it reaches an end position and can be displaced in an opposite second rotational direction, wherein the dose metering member is coupled to the delivery device in such a way that the latter, when actuated, dispenses the product dose that has been selected by the dose metering member;
a dosing and activating element that can be rotated about and linearly shifted along a longitudinal axis in and counter to an advancing direction, wherein the dosing and activating element comprises a cylindrical portion around the conveying means and a portion that extends beyond the rear housing section, and wherein the dosing and activating element protrudes into the dose metering member; and
at least one stop and at least one counter-stop, one of which is associated with one of the housing sections and the other is formed by the dose metering member, wherein the stop and the counter-stop come to rest against one another in the end position to prevent the rotational displacement of the dose metering member in the first rotational direction from continuing beyond the end position.

22. An injection apparatus with a first and second end position-blocked dosing setting member, said injection apparatus comprising:
a) a casing comprising a reservoir for an injectable product;
b) a conveying means using which a selected product dosage can be delivered from said reservoir;
c) a dosage setting member which rotates in order to select said product dosage and can perform a rotational movement in a first rotational direction up to a first end position and in an opposite, second rotational direction relative to said casing up to a second end position, said dosage setting member coupled to said conveying means such that when activated, the conveying means delivers the product dosage selected by said dosage setting member; and
d) a dosing and activating element that can be rotated about and linearly shifted along a longitudinal axis in and counter to an advancing direction, wherein the dosing and activating element comprises a cylindrical portion that surrounds the conveying means and said dosing and activating element extends beyond the casing, wherein a section of the dosing and activating element protrudes into the dosage setting member;
e) a first and a second rotational block, each rotational block comprising one or more rotational stoppers and one or more rotational counter stoppers, the one or more rotational stoppers or the one or more rotational counter stoppers formed by the casing and the other formed by the dosage setting member;
f) wherein said at least one rotational stopper and said at least one rotational counter stopper of the first rotational block abut against each other in the first end position in said first rotational direction, in order to prevent the dosage setting member from rotating in the first rotational direction beyond the first end position; and
g) wherein said at least one rotational stopper and said at least one rotational counter stopper of the second rotational block abut against each other in the second end position in said second rotational direction, in order to prevent the dosage setting member from rotating in the second rotational direction beyond the second end position.

23. The injection apparatus set forth in claim 1, wherein the casing comprises a front casing section and a rear casing section, said front and rear casing sections non-rotationally and non-shiftably connected.

24. The injection apparatus set forth in claim 1, wherein the dosage setting member and dosing and activating element are generally coaxial.

25. The injection apparatus according to claim 17, further comprising a rear casing section, wherein one of the at least one rotational stopper and at least one rotational counter stopper is associated with the rear casing section.

26. The injection apparatus according to claim 17, further comprising a rear casing section, wherein the dosing and activating element can be rotated about and linearly shifted along the longitudinal axis relative the rear casing section, and wherein one of the at least one rotational stopper and at least one rotational counter stopper is associated with the rear housing section.

27. The injection apparatus according to claim 17, wherein a rear area of the dosage setting member forms a translational stopper for the dosing and activating element.

* * * * *